(12) United States Patent
Littleton et al.

(10) Patent No.: US 10,709,819 B2
(45) Date of Patent: Jul. 14, 2020

(54) METHOD FOR COATING CATHETERS WITH A LAYER OF ANTIMICROBIAL AGENT

(71) Applicant: ValenCide, San Diego, CA (US)

(72) Inventors: Kermit R. Littleton, Ellijay, GA (US); Lynn R. Detlor, Ramona, CA (US); Albert Rego, Mission Viejo, CA (US)

(73) Assignee: VALENCIDE LLC, San Diego, CA (US)

(*) Notice: Subject to any disclaimer, the term of this patent is extended or adjusted under 35 U.S.C. 154(b) by 0 days.

(21) Appl. No.: 15/711,424

(22) Filed: Sep. 21, 2017

(65) Prior Publication Data

US 2019/0083682 A1     Mar. 21, 2019

(51) Int. Cl.
| | |
|---|---|
| *A61L 29/16* | (2006.01) |
| *A61F 2/26* | (2006.01) |
| *A61L 27/54* | (2006.01) |
| *A61L 31/08* | (2006.01) |
| *A61L 29/04* | (2006.01) |
| *A61L 29/08* | (2006.01) |
| *A61M 25/00* | (2006.01) |

(52) U.S. Cl.
CPC .............. *A61L 29/16* (2013.01); *A61F 2/26* (2013.01); *A61L 27/54* (2013.01); *A61L 29/042* (2013.01); *A61L 29/085* (2013.01); *A61L 31/08* (2013.01); *A61L 2300/202* (2013.01); *A61L 2300/404* (2013.01); *A61L 2300/406* (2013.01); *A61L 2300/608* (2013.01); *A61L 2420/02* (2013.01); *A61L 2420/08* (2013.01); *A61M 25/0009* (2013.01); *A61M 25/0017* (2013.01); *A61M 2025/0056* (2013.01)

(58) Field of Classification Search
CPC .......................................................... A61L 29/16
See application file for complete search history.

(56) References Cited

U.S. PATENT DOCUMENTS

| | | |
|---|---|---|
| 4,010,259 A | 3/1977 | Johansson |
| 4,381,380 A | 4/1983 | Leveen |

FOREIGN PATENT DOCUMENTS

WO    WO-2010124130 A2 * 10/2010    ............. A01N 59/12

OTHER PUBLICATIONS

Luo et al. ("Antimicrobial Activity and Biocompatibility of Polyurethane—Iodine Complexes." Journal of Bioactive and Compatible Polymers, vol. 25, No. 2, Mar. 2010, pp. 185-206) (Year: 2010).*

* cited by examiner

*Primary Examiner* — Benjamin J Packard
(74) *Attorney, Agent, or Firm* — Aileen Law; Oppedahl Patent Law Firm LLC (57) ABSTRACT

Disclosed is a catheter with an antimicrobial coating that reduces the development of device-associated urinary tract, respiratory and bloodstream infections and methods for making the same. The disclosed method comprises the layered application of one or more organic solutions to a coatable elastomeric product which results in a device that allows for a controlled time release of iodine therefrom. Application of one or more antitoxic agents in multiple layers and locations on the desired elastomeric product helps to tailor delivery and potency of the antimicrobial coating.

21 Claims, 6 Drawing Sheets

METHOD FOR COATING CATHETERS WITH A LAYER OF ANTIMICROBIAL AGENT

FIELD

The present invention relates to urological catheters, known as Foley bladder catheters and other medical catheter related devices such as dialysis catheters and cardiac catheters as a few examples. In particular, the present invention relates to catheters and implantable devices that are coatable with an iodinated polymer iodine released anti-infective, programmable polymeric dispersion for inhibiting infection induced by the catheters which are disposed and positioned in a human body.

BACKGROUND OF THE INVENTION

Catheters are commonly utilized especially by physicians and other health care personnel for various purposes, such as the long and short term intravenous delivery (infusion) and withdrawal of fluids, such as urine, Dialysis catheters, as well as blood and blood products for treatment and monitoring of the patient. Examples of catheters include urinary catheters, suction catheters, dialysis catheters, venous catheters, Swan-Ganz catheters, double and triple lumen central catheters, arterial catheters, arterial line monitoring catheters, to name but a few.

The widespread use of respiratory catheters, venous and or arterial catheters, urological catheters, and dialysis catheters has resulted in dangerous infections owing to the adherence and colonization of pathogens on the catheter surface. Moreover, colonized catheters may produce a reservoir of antimicrobial resistant microorganisms. Catheter-associated urinary tract infections are now the most common type of hospital acquired infections. Catheter-related bloodstream and respiratory infections are also very common and often result in morbidity. Antimicrobial catheters currently on the market have been shown to offer some degree of protection against dangerous microbes. These catheters use various active agents such as ionic silver, chlorhexidine and antibiotics. However, commercially available antimicrobial catheters have considerable drawbacks including a narrow range of antibacterial activity, little to no delivery controls and the potential to cause undesirable side effects when drug-based coatings such as ionic silver, chlorhexidine and antibiotics are used. Silver coatings, in particular have limited antibacterial effectiveness. Furthermore, development of bacterial resistance against drug based active agents from microbial mutations is well-known, rendering them ineffective.

Iodine is a well-known broad spectrum antimicrobial agent that has bactericidal, fungicidal and virucidal properties which has been used for over centuries as an antiseptic. When iodine reacts with aqueous solutions, free iodine, which provides the germicidal effect, is released. The control of the free iodine is dependent on the acidity of the coating as exemplified herein. Therefore, the pH range of the coating will determine whether the iodine is available for antimicrobial effectiveness. While generally inhibiting infective germs over the short term, the biocidal effectiveness of iodine is dependent on, inter alia, how long the infective agent is exposed to the iodine in the pH modified coating.

To increase the effectiveness of iodine, it is normally combined with a solubilizing agent or other carrier to form an iodophor. Such iodophors, in effect, provide a reservoir of iodine from which small amounts of free iodine in aqueous solution are released over a period of time. These iodophors formulated for example, as a solution, soap, cream or paste, are then topically applied to that area of a patient's body which is desired to be treated. Perhaps the best known of these iodophors is povidone-iodine solution in liquid form, in which iodine in the form of triiodide is complexed with the polymer polyvinylpyrrolidone. An example of such an application can be found by reference to U.S. Pat. No. 4,010,259.

It has also been disclosed in U.S. Pat. No. 4,381,380 issued to Le Veen et al, to provide cross-linked thermoplastic polyurethane articles, such as catheters, into which iodine (12) has been complexed for antibacterial use. While being useful for their purpose, such cross-linked thermoplastics cannot be utilized for coatings nor do they provide the same level of antibacterial protection. The encapsulation of the iodophor in polyurethanes is problematic in that the iodine cannot be released and is therefore not available for delivery in a controlled manner. Stated differently, the iodine (12) is imbedded within the polymer and is not available to react as an effective antimicrobial. A particular problem often faced with antimicrobial coated elastomeric catheters is that the biocidal material (volatile 12) may leach from the surface of the elastomeric product. Hence, the antimicrobial efficacy is significantly reduced over time. Moreover, such leaching may create significant problems, particularly when the elastomeric products are used in medical applications, for example, when proteins are present with 12 in latex or in elastomeric products with double bonds (imparting elastic deformation).

Another problem comes when the antimicrobial agent is directly incorporated into the underlying elastomeric material. While this can reduce leaching of iodine located on the surface of the elastomeric product, it also necessitates a relatively large amount of iodine be incorporated in order to exert a significant toxic effect on a broad spectrum of pathogens. The use of polymer coatings to incorporate iodine has the effect of trapping the iodine such that there is also a need for relatively large amounts of iodine to be incorporated in order to exert a significant toxic effect.

The present device has the ability to apply iodine in the form of polyiodides in a coating process which incorporates the antimicrobial agent only into the relatively thin outer coating layer that nonetheless provides for a steady release of iodine solely at the surface of the device.

The present device provides for a catheter which has a thermoset uncross-linked polymer coating that has iodine either complexed therein for quick and relative immediate release of the iodine and/or matrixed therein for sustained release of the iodine on the surface coating of said catheter.

Thus, it can be seen that there remains a need for catheters that are solvent coatable with a polymeric dispersion or solution that have iodine complexed and/or matrixed therein, so as to provide for immediate and/or sustained release of the iodine for inhibiting microbial growth, that is commonly associated with the use of such catheters.

Elastomeric materials have proven to be very valuable in many healthcare and medical applications. Several types of elastomeric polymers have properties which are ideal for such applications. For instance, materials such as latex, silicone and polyvinyl demonstrates a combination of softness, high tensile strength and excellent film-forming properties.

Hence, there is a need to develop new antimicrobial contact kill type products, where such catheters are effective against all currently known microorganisms, are nontoxic and are inexpensive to manufacture.

Polyiodide resins have proven to be as much as 1,000,000 times more effective than an iodine (12) molecule alone. A large number of chemical, biochemical, and physiological studies have proven that the iodine added to microorganisms is irreversibly bound. This has the effect of devitalizing the microorganisms by damaging cellular proteins, lipids, enzymes, oxidation of sulfhydryl groups and other chemical pathways.

Microorganisms carry a negative electrical potential energy on their surface when damp with water. The polyiodide resin carries a positive electrical potential charge. The microorganisms with their negative electrical potential are naturally drawn to the iodinated resin particles with their positive electrical potential charge, thus ensuring contact kill. The iodinated resin releases the correct lethal dose of nascent iodine in less than 3 seconds at a body temperature 98.6° F. or 36.9° C.

The ion-exchange resin bead or particle is chemically bonded homogeneously with polyiodide of uniform composition throughout its interior. As nascent iodine is consumed more is continuously fed to the surface from the interior of the resin bead or particle.

The unique release on demand feature of polyiodide resin can be demonstrated by adding resin beads to the well of a depression microscope slide with a suspension of the highly motile ciliate Tetrahymena pyriformis. When observed microscopically, individual cells maintain their motion while swimming in a solution with 2 ppm of iodine residual. However after a collision with a resin bead, their activity dramatically slows and within seconds stops altogether.

Bacteria, viruses, yeast, fungi, and protozoa are not able to develop resistance to iodine even after a period of prolonged exposure to polyiodinated resins. It is not expected that emerging new microbial organisms will develop resistance to iodine, as historically there has been no development of resistance to iodine, as well as polyiodinated resin.

SUMMARY OF THE INVENTION

Brief Description of the Drawing(s) and Charts

DETAILED DESCRIPTION OF THE INVENTION

The following sections describe exemplary embodiments of the present invention. It should be apparent to those skilled in the art that the described embodiments of the present invention provided herein are illustrative only and not limiting, having been presented by way of example only.

Throughout the description, where items are described as having, including, or comprising one or more specific components, or where processes and methods are described as having, including, or comprising one or more specific steps, it is contemplated that, additionally, there are items of the present invention that consist essentially of, or consist of, the one or more recited components, and that there are processes and methods according to the present invention that consist essentially of, or consist of, the one or more recited processing steps.

Scale-up and/or scale-down of systems, processes, units, and/or methods disclosed herein may be performed by those of skill in the relevant art. Processes described herein are configured for batch operation, continuous operation, or semi-continuous operation.

The present invention relates generally to coating of elastomeric products with an antimicrobial material, and methods of making the same. The antitoxic agent is preferably an antimicrobial agent, an antiviral agent, a biochemical agent or a reducing agent. The active agent preferably exerts a toxic effect on a diverse array of microorganisms and other pathogens and environmental toxins while not being toxic to the user. Preferably, the antitoxic agent comprises polyiodinated resin particles.

Disinfectants are known in the art. In one embodiment, polyiodinated resins made by Hybrid Technologies Corporation was used. The particle sizes of the powders used range from about 1 micron to about 150 microns. Preferably, the particle sizes should be in the range from about 5 microns to about 10 microns.

Iodinated resins used in accordance with the present invention are referred to as polyiodinated resin. The base polymer used to manufacture such polyiodinated resins is a strong base anion exchange resin. These resins contain quaternary ammonium exchange groups which are bonded to styrene divinylbenzene polymer chains. Polyiodinated resins can be made with different percentages of iodine and may be used in accordance with the present invention. Different percentages of iodine in the polyiodinated resins will confer different properties to the resin, in particular, different levels of biocidal activity. The particular resin used is based on the desired application and locations on the catheter. For example, two different polyiodinated resins could be used on two different exterior locations on the catheter as well as a third different polyiodinated resin could be used on the interior of the catheter. The varied resin coatings allow the catheter to administer different levels of iodine from each location as desired, which results in a controlled delivery and enhances the duration of the antimicrobial efficacy.

As disclosed herein, the catheter is prepared by coating with thermoplastic and hydrophilic polyurethanes in a tetrahydrofuran solution and allowing the catheter to dry. A polyiodinated resin powder that had been dispersed in a tetrahydrofuran/acetone solution with the polyurethane is applied and then allowed to dry to form a solid coating. The solutions may be applied by dipping the catheter in the liquid.

Tetrahydrofuran solutions of polyurethane are dipped/placed onto the underlying catheter surface, which is allowed to dry. One or more layers can be implemented. A tetrahydrofuran/acetone solution of the antimicrobial resin is then applied (e.g., sprayed or dipped) onto the polyurethane coating and allowed to dry. The coating process prevents adherence and colonization of pathogens on the catheter surface due to the added antimicrobial properties of the iodinated resin. Hence, the catheters made by the coating process of the present invention significantly reduce the development of catheter-associated urinary tract, respiratory and bloodstream infections, without compromising the performance of the catheter for its intended use.

As discussed in the Background section, a particular problem often faced with antimicrobial coated elastomeric catheters is that the biocidal material may leach from the surface of the elastomeric product. Hence, the antimicrobial efficacy is significantly reduced over time. Moreover, such leaching may create significant problems, particularly when the elastomeric products are used in medical applications. In contrast, the polyiodinated resin incorporated in the coating disclosed herein does not have a tendency to leach or rub off of the surface.

Another significant advantage of the present invention is that a relatively small amount of the antimicrobial agent need be applied in order to exert a significant toxic effect on a broad spectrum of pathogens. Unlike methods in the prior art, in which the antimicrobial agent is directly incorporated into the underlying elastomeric material, the present invention involves the coating process which incorporates the antimicrobial agent only into the relatively thin outer coating layer. As such, the amount of antimicrobial agent needed to demonstrate antimicrobial efficacy is significantly lessened (Reference U.S. Pat. No. 4,381,380).

With regards to efficacy, the elastomeric materials made with the coating process of the present invention have been tested against a robust organism *Pseudomonas aeruginosa* utilizing a modification of a recognized standard: AATCC Method 100 (modified for twenty-four hour repeat insult testing) and ASTM E2149 (modified for twenty-four hour repeat insult testing). It is well-known in the industry that a log reduction is a 10-fold reduction in bacteria, meaning the disinfectant reduces the number of live bacteria by 90 percent for every step. The test results disclosed herein showed an average reduction of greater than $10^6$ in bacterial count vs. untreated samples. The present system exceeds the FDA 4-log reduction requirement for medical devices, meaning a 4-log kill reduces the colony to 100 bacteria after a 99.99% reduction.

With regards to efficacy, the elastomeric materials made with the coating process of the present invention have been tested against a robust organism *Staphylococcus aureus* utilizing the following recognized standard: AATCC Method 100 (modified for twenty-four hour repeat insult testing). The test results showed an average reduction of greater than $10^6$ in bacterial count vs. untreated samples.

The methodology described above for producing antimicrobial-coated catheters such as urinary, cardiac, and dialysis, may also be used to coat a host of other articles such as stents and tubing.

The examples disclosed herein illustrate various aspects and embodiments of the present invention. They are not to be construed to limit the claims in any manner whatsoever.

Definitions

Catheter—a thin tube made from medical grade materials serving a broad range of functions. Catheters are medical devices that can be inserted in the body to treat diseases or perform a surgical procedure. By modifying the material or adjusting the way catheters are manufactured, it is possible to tailor catheters for cardiovascular, urological, gastrointestinal, neurovascular, and ophthalmic applications.

Polyiodide—Molecular iodide of more than one iodine atom containing a net negative charge Antimicrobial—An agent that kills microorganisms or inhibits microbial growth.

Elastomeric—A polymer with viscoelasticity (having both viscosity and elasticity) and very weak inter-molecular forces, generally having low Young's modulus and high failure strain compared with other materials.

Ion-Exchange—An exchange of ions between two electrolytes or the exchange of ions of the same charge between an insoluble solid and an electrolyte solution.

A. EMBODIMENTS

A new method of manufacturing catheters coated with antimicrobial agents is described herein. The methodology involves coating an elastomeric catheter with layers of polyurethane dissolved in tetrahydrofuran, which is then allowed to dry, thereafter affixed with an antimicrobial agent via a tetrahydrofuran/acetone solution. In preferred embodiments, the antimicrobial agent is a demand release antimicrobial contact disinfectant polyiodinated resins with the ability to be tailored to specific medical needs based on the concentration of iodine in its various forms such as $I_3^-$, $I_5^-$, $I_7^-$.

The coating process may be performed without (or with minimal) application of heat, thereby avoiding deactivation of the antimicrobial agent, yet still achieving stable adherence of the coating to the catheter. Further, it is found that a very thin coating containing a polyiodinated resin as antibacterial agent is sufficient to achieve excellent antimicrobial properties without adversely impacting the performance properties of the product (e.g., flexibility and strength). The polyiodinated resin serves as an antimicrobial agent which prevents or greatly inhibits hazardous microbes that catheters contact from spreading to any surfaces or liquids that are touched. The product once treated by the process has proven to maintain its kill capabilities beyond 96 hours (repeated inoculation every 24 hours with >$10^7$ *Pseudomonas aeruginosa* for the entire study) as referenced by test results done by Wuxi AppTec, a third party reference lab.

The invention relates to elastomeric products, which may include catheters that are coated with a thin layer of elastomeric polymeric coating containing an antimicrobial agent, particularly a demand disinfectant polyiodinated resin. The elastomeric product can be coated with elastomeric substance (coating) comprised of a different material and is not restricted to the same identical materials. The antimicrobial-coated catheters are prepared by adding thermoplastic and hydrophilic polyurethane as a polymer coating via a tetrahydrofuran solution of the polyurethanes, and then affixing the antitoxic agent via a tetrahydrofuran/acetone solution. The antimicrobial coatings are capable of providing a high level of protection against microbes and other many biohazards, such as viruses, bacteria, fungi, and molds.

In one aspect, the invention is directed to an elastomeric product with enhanced antimicrobial properties, the product comprising: a foundation material; and a coating applied over the foundation, antimicrobial resin affixed to the coating.

In certain embodiments, multiple coatings comprising polyurethane can be used. The coating may advantageously have a thickness in various ranges for set properties, duration and efficacy over differing periods of time, from 5 μm up to and including 250 μm.

In certain embodiments, the catheter has coatings of different polyiodides in different locations on or in the device. As examples, triiodide may be applied in one location, pentaiodide may be applied in a different location on an exterior surface; one polyiodide may be situated at the tip of the device, or on the outside surface of the device, and another polyiodide may be situated on another location or in an inner exposed surface of the device.

Triiodide may be used as a low level antimicrobial exposure and the pentaiodide may be used as a high level antimicrobial exposure to achieve the preferred antimicrobial effectiveness profile over time. The triiodide and pentaiodide levels may be tailored for specific antimicrobial effectiveness profiles as needed.

In certain embodiments, the catheter coatings on its exterior or interior surfaces of the catheter can be a blend of polyiodides, for example triiodide and pentaiodide in the range of 80%-98% $I_3^-$, and 2%-20% $I_5^-$.

In certain embodiments, the polyiodinated resin particles advantageously have an average size within the range from 5 μm to 50 μm.

In certain embodiments, the polyiodinated resin particles advantageously have a concentration in the range of 2 wt. % to 25 wt. %.

In yet another aspect, the invention is directed to a medical catheter which is coated with a layer of an elastomeric polymer to which polyiodinated resin particulates are dispersed. The coating provides a significant amount of protection against a broad array of biocidal agents and other potential biohazards.

Another aspect of the present invention is directed to antimicrobial coatings for elastomeric products comprising an elastomeric polymer selected from the group consisting of latex rubber and other elastomeric materials and a plurality of polyiodinated resin particles incorporated on the surface of the elastomeric polymer, wherein the thickness of the coating is in the range from about 20 μm to about 100 μm.

Elements of embodiments described with respect to a given aspect of the invention may be used in various embodiments of another aspect of the invention (e.g., subject matter of dependent claims may apply to more than one independent claim).

B. IP INFORMATION FOR FILING APPLICATION PATENT

1. A polymer type barrier coating (a barrier coating was selected in an effort to prevent or minimize iodine from migrating into the base Natural Rubber Latex (NRL) catheter substrate and to serve as a coating to which a secondary polymer could be solvent bonded).
   a. Medical grade aliphatic, polyester-based hydrogel; medical grade aliphatic, polyester-based solution medical grade aliphatic and medical grade aromatic polymers were evaluated for their ability to adhere to the base catheter in a stirred water bath at 35° C.-42° C. for an extended period of up to 72 hours.
   b. The barrier polymer, a polyurethane with high water absorption characteristics, exhibited definite signs of separating from the substrate NRL under the above prescribed laboratory conditions.
2. A polymer concentration of polymer with specific properties was evaluated from a range of 2.5% wt./wt. and 5.0% wt./wt. in solvent and found that the higher concentration of 5.0% was cloudy, which indicated unsatisfactory dissolution of the polymer in THF. Dipping of samples also exhibited a surplus of polymer at the distal end of the sample that tended to run back when held in a horizontal position and rotated to dry.
   a. The concentration was reduced to 2.5% wt./wt. in THF with 2.5% being selected as optimum in the amount required to provide a sufficient quantity to bind a secondary polymer, prevent visual (microscopically) stress cracks in the substrate surface and provide rapid drying and more even flow (minimize buildup at distal end of sample) upon extraction.
   b. 1 and 2 dips of clear grade polyether-based thermoplastic polyurethane were evaluated due to potential economy of manufacture and 2 dips provided a more satisfactory coating for the adhesion of a secondary polymer (to facilitate binding of polyiodide) and a barrier coat between the polyiodide and substrate catheter.
   c. Test specimens prepared for biological efficacy were prepared using 2 dips of clear grade polyether-based thermoplastic polyurethane at 2.5% wt./wt. in THF as the tie coating that was applied to the NRL catheter sample.
   d. A clear grade polyether-based thermoplastic polyurethane @ 2.5% wt./wt. in THF: 400 g×0.025=10 g clear grade polyether-based thermoplastic polyurethane+390 g THF (or 439 ml) stirred at moderate rpm (sufficient to create approximately a 1.25 in.-1.5 in. deep vortex) for approximately 12 hours until completely dissolved.
3. Polymer type for binder coating (the polyiodide is not mixed into the polymer as encapsulation of the polyiodide is not desired. The polymer is used to anchor the polyiodide particulates to a sufficient degree as to prevent the particulates from rubbing or flaking off when handled but not to the degree as to encapsulate them in a coating of polymeric material).
   a. A thermoplastic polyurethane with an aliphatic, hydrophilic polyether-based resin formulated to absorb equilibrium water contents from 20% to 1000% of the weight of dry resin was evaluated as a binder coating by applying to catheter samples previously coated with clear grade polyether-based thermoplastic polyurethane for adhesion to the barrier/tie coating by using the water bath technique described in (1.a) above. There was no apparent loss of polymer in the water bath as evidenced by lack of cloudiness or particulates present.
   b. A thermoplastic polyurethane with an aliphatic, hydrophilic polyether-based resin formulated to absorb equilibrium water contents from 20% to 1000% of the weight of dry resin @1.5% wt./wt. in THF: 350 g×0.015=5.25 g said thermoplastic polyurethane with an aliphatic, hydrophilic polyether-based resin+344.8 g (387.7 ml) THF stirred at moderate rpm (sufficient to create approximately a 1.25 in.-1.5 in. deep vortex) stirred over night to assure complete dissolution of polymer and add sufficient citric acid to bring pH to 3.0-3.4.
   c. This coating was dipped 2× over the coatings of clear grade polyether-based thermoplastic polyurethane for attachment of the polyiodide particulates.
   d. Polyiodide 10 μm was suspended in THF using a 12% suspension of the polyiodide in THF:acetone at a ratio of 2:4. A thermoplastic polyurethane with an aliphatic polyether-based resin formulated to absorb equilibrium water contents from 20% to 1000% of the weight of dry resin was evaluated for iodine neutralization (visual absence of color) after polyiodide was dipped onto said thermoplastic polyurethane with an aliphatic, hydrophilic polyether-based resin in (b.) above. The sample was placed under the microscope at 40× magnification and 1 drop of 0.1 N $NA_2S_2O_3$ was placed on the visual surface and the timer started. After 60 minutes there was no visual sign of color change from the $NA_2S_2O_3$. This solution was dissolving said thermoplastic polyurethane with an aliphatic, hydrophilic polyether-based resin and the solvents were adjusted to 2:5 ratio THF:acetone and decreased.
   e. The 2:5 ratio THF:acetone reduced the polyiodide concentration to 10.1%.
   f. The $NA_2S_2O_3$ neutralization of this formulation showed visual neutralization initiated in 5 minutes and was completed in 60 minutes.
4. Samples for microbiological efficacy were then prepared using the polyether-based thermoplastic polyurethane clear grade formulation from (2.d.) above as the barrier/tie coat; The thermoplastic polyurethane with an aliphatic, hydrophilic polyether-based resin binder coating from (3.b.) above and a 10% polyiodide, I0 μm suspension in a solvent blend ratio of 2:5 THF:acetone.
   a. All coatings were applied under laboratory hand dipped techniques using 2× dips for each of the formulations.
      i. The clear grade polyether-based thermoplastic polyurethane was air dried in a HEPA hood overnight after coating and prior to application of said thermoplastic polyurethane with an aliphatic, hydrophilic polyether-based resin.
      ii. The thermoplastic polyurethane with an aliphatic, hydrophilic polyether-based resin coating was dried in the HEPA hood overnight after coating and prior to application of the polyiodide suspension.
      iii. The polyiodide dips were allowed to dry overnight and then packaged for microbiological testing.
5. There was a greater than 4-log reduction ($1.0 \times 10^1$ CFU) in microorganisms when the product was inoculated with *Pseudomonas aeruginosa* ATCC 9027 at $1.9 \times 10^5$ over twenty-four hours per (WuXi AppTec Report Number 823213).
6. Once the results were received from WuXi AppTec, and were favorable, efforts to improve the overall efficiency of the samples were continued.
7. The polyiodide concentration was considered to be insufficient and that the solvent ratio was maybe just a little too weak to bind sufficient polyiodide to the thermoplastic polyurethane with an aliphatic, hydrophilic polyether-based resin.
   a. The concentration of polyiodide I0 μm was increased to 12% wt./wt. in a 2:5 ratio THF:acetone and applied to samples prepared with 2× dips of clear grade polyether-based thermoplastic polyurethane and 2× dips of said thermoplastic polyurethane with an aliphatic, hydrophilic polyether-based resin.
   b. Neutralization of iodine with the technique described in (3.d.) above indicated neutralization was visually initiated in 7 minutes and completed in 40 minutes.
   c. Samples were prepared for microbiological efficacy testing and sent to WuXi AppTech.
8. There was a greater than 4-log reduction ($1.0 \times 10^1$ CFU) in microorganisms when the product was inoculated with *Pseudomonas aeruginosa* ATCC 9027 at $1.9 \times 10^7$ over twenty-four hours per (WuXi AppTec Report Number 826515)
9. In conversations with WuXi AppTech microbiologists, it was deemed a high probability that 72-96 hours in a wrist action shaker flask would create natural die off of the microbial agent. *Pseudomonas aeruginosa* was utilized and is considered an excellent model for evaluation of efficacy due to its ruggedness and its resistance to antimicrobial agents. Therefore, a viability test was performed utilizing a reduced shaker speed.
   a. There was no reduction in microorganisms which demonstrated that the viability of the techniques was valid per (WuXi AppTec Report Number 828085.A01).
10. Continuing in an effort to improve the overall microbiological, the solvents were adjusted to 2:4.5 ratio of THF:acetone.
    a. Neutralization was again observed to initiate in 5 minutes and was complete in 30 minutes using the technique described in (3.d) above.
11. Samples were then prepared for the 72 hour microbial efficacy testing utilizing a thermoplastic polyurethane with an aliphatic, hydrophilic polyether-based resin dip solution with pH=3.26 and a polyiodide, I0 μm suspension in 2:4.5 ratio of THF:acetone with pH=3.24.
12. There was a greater than 6.1 log reduction ($1.0 \times 10^1$ CFU) in microorganisms when the product was inoculated with *Pseudomonas aeruginosa* ATCC 9027 at $1.63 \times 10^7$ over a seventy-two hour period per (WuXi AppTec Report Number 831569.A01).

C. EXAMPLES

These examples may or may not require modifications to current existing manufacturing and process equipment. The examples are intended to demonstrate that a finished product can be produced in an existing manufacturing process that is further processed with one or two additional dipping and coating steps.

Preparation of Catheter for Coating

1) Take a commercially available catheter and soak in silicone remover solvent for about 5 hours to ensure the complete removal of added coating on the base polymeric material.
2) Rinse the catheter under water to remove all of the silicone remover solvent and allow it to completely dry at room temperature.
3) When dried, remove all additional coatings to reach the base polymeric material and ensure that the surface of the catheter is free of particles.
4) Place a rod (metal or plastic) in the middle of the catheter to allow for more rigidity during the coating process.

Preparing the Barrier Polyurethane Coating

1) A polyurethane polymer is used as a barrier between the resin and the underlying catheter. This is prepared by making a 2.5% wt./wt. solution in tetrahydrofuran by adding the polymer to the tetrahydrofuran with moderate stirring at 35° C.-42° C. until completely dissolved.
2) The resultant solution is then applied by dipping the prepared catheter (with each end plugged or unplugged) into the solution as follows: The catheter is rotated in the horizontal position at a speed of 3-4 rpm for 5 minutes to facilitate evaporation and even distribution of the polymer.

Figure 1:
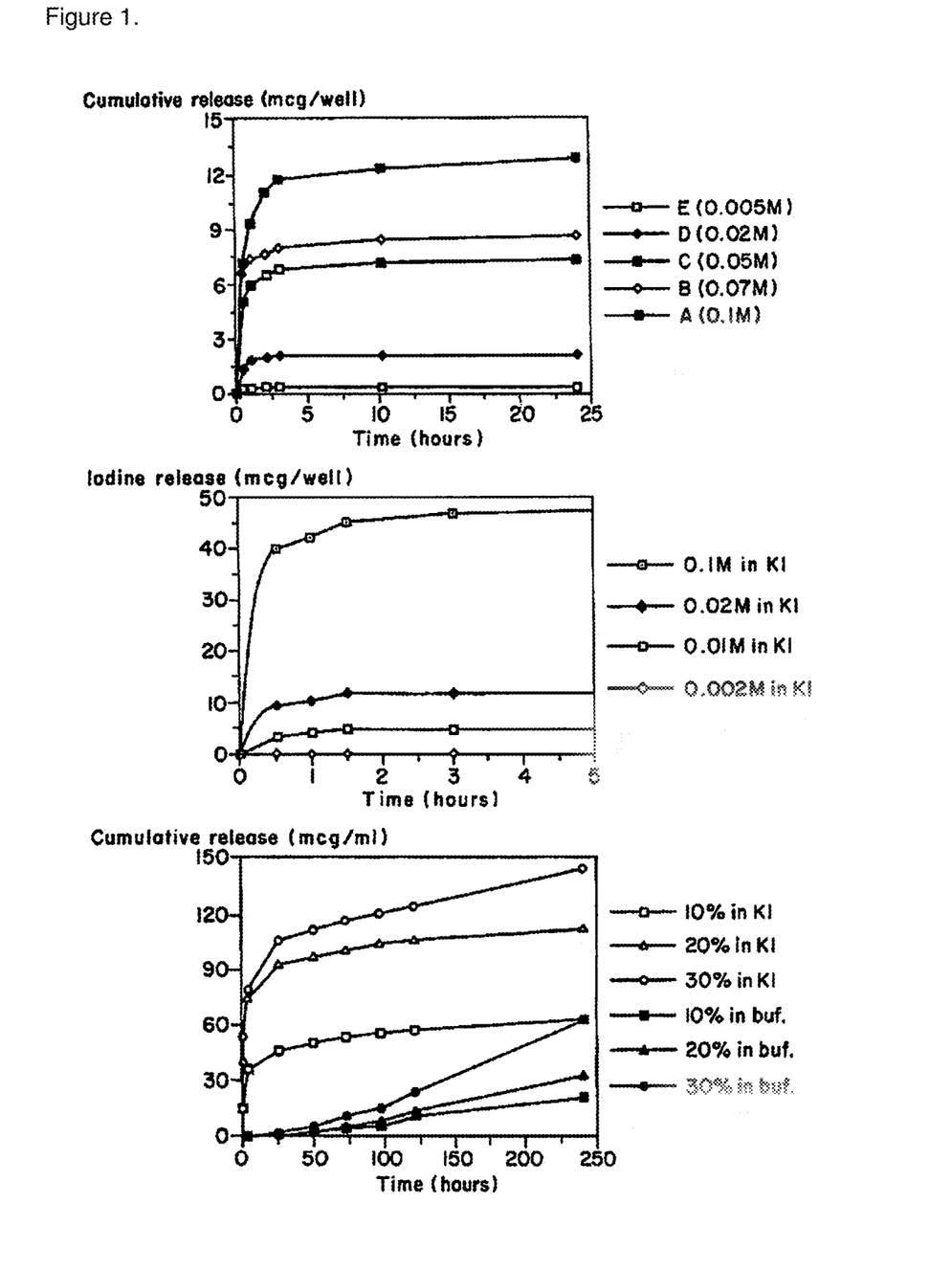
FIG. 1. Release rates from previous studies.
Figure 2:
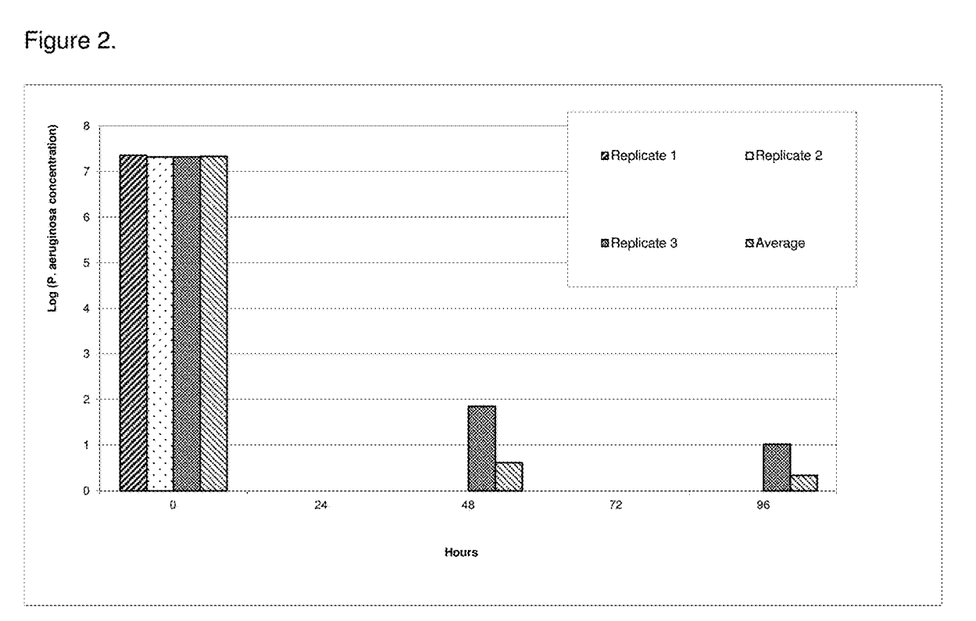
FIG. 2 Graph showing biological performance of latex/iodinated resin coated latex elastomers of the present invention against the challenge microorganism *Pseudomonas aeruginosa*, with re-inoculation every twenty-four hours up to ninety-six hours per (WuXi AppTec Report Number 901978).
Figure 3:
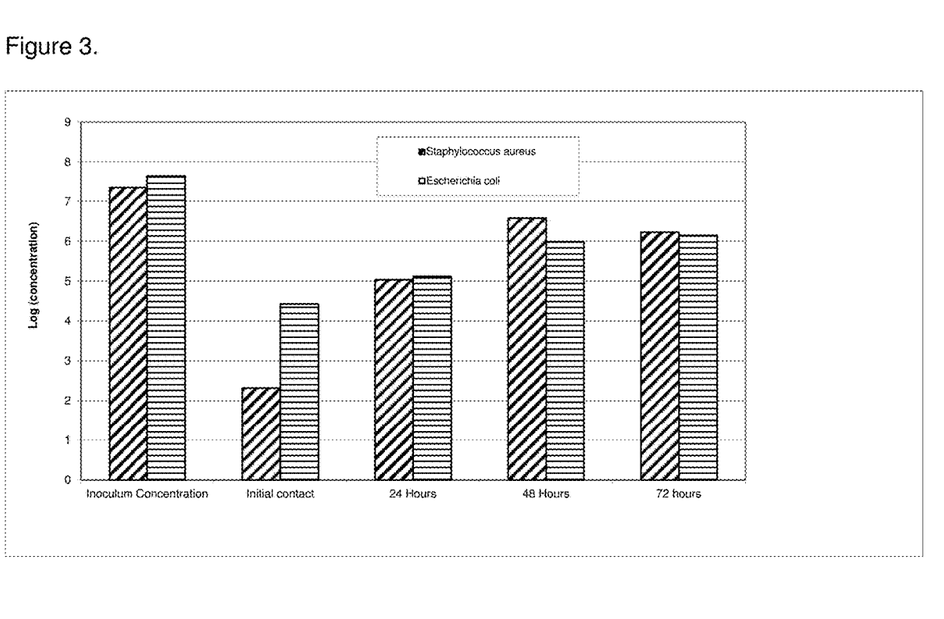
FIG. 3 Graph showing biological performance of latex/iodinated resin coated latex elastomers of the present invention against the challenge microorganisms *S. aureus* and *E. coli* per (WuXi AppTec Report Number 793489).
Figure 4:
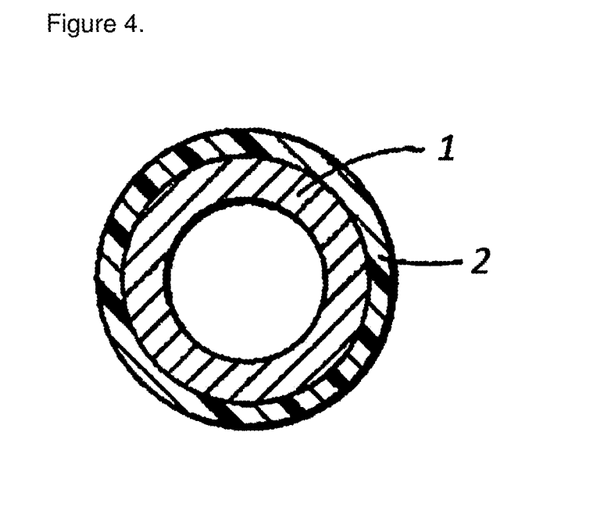
FIG. 4 Cross section of catheter, 1, with barrier polyurethane coating applied, 2. Only the outside coating is shown for the purpose of clarity.
Figure 5:
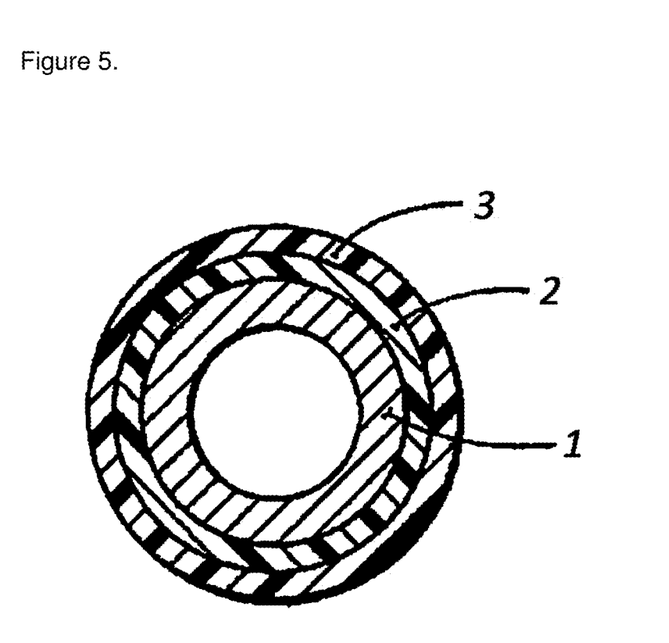
FIG. 5 Cross section of catheter, 1, with binder polyurethane coating, 3, applied on top of barrier polyurethane coating, 2. Only the outside coating is shown for the purpose of clarity.

3) The catheter is allowed to dry in a HEPA-filtered hood or similar environment. See FIG. 5.

Preparing the Binder Polyurethane Coating

Figure 6:
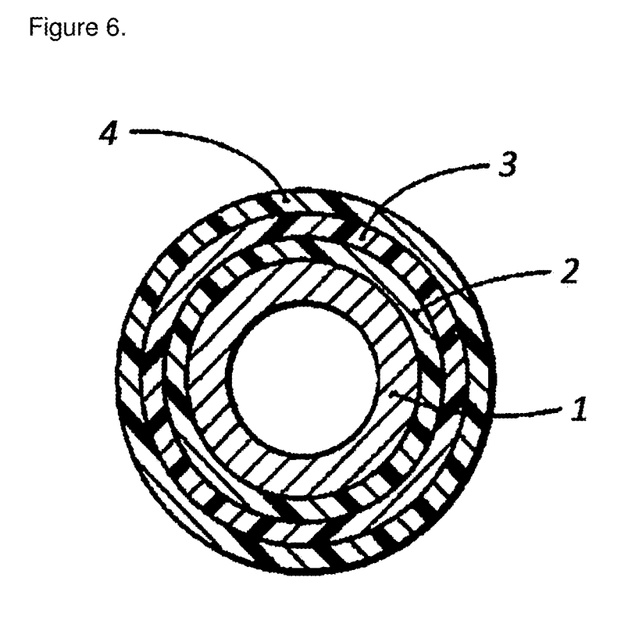
FIG. 6 Cross section of catheter, 1, with Antimicrobial resin layer, 4, on top of both binder polyurethane coating, 3, and barrier polyurethane coating, 2. Only the outside coating is shown for the purpose of clarity.

1) A layer of polyurethane polymer is used as a binder between the resin and the barrier polyurethane layer. This is prepared by making a 1.5% wt./wt. solution in tetrahydrofuran by adding the polymer to the tetrahydrofuran and moderately stirring until completely dissolved with 350 g×0.015=5.25 g of a thermoplastic polyurethane with an aliphatic, hydrophilic polyester-based resin which has been formulated to absorb equilibrium water contents from 20% to 1000% of the weight of the dry resin+344.8 g (387.7 ml) THF stirred at a moderate rpm (sufficient to create approximately a 1.25 in.-1.5 in. deep vortex).
2) The pH of the solution was adjusted to between 3.0 and 3.4 with citric acid.
3) The resultant solution is then applied by dipping the prepared catheter into the solution, or by spraying the solution onto the catheter as follows: The catheter is rotated in the horizontal position at a speed of 3-4 rpm for 5 minutes to facilitate evaporation and even distribution of the polymer.
4) The catheter was allowed to dry in a HEPA-filtered hood or similar environment.
5) The solution is reapplied an additional time to the catheter and allowed to dry as previously described. See FIG. 6.

Preparation of the Antimicrobial Resin Coating

1) A mixture of antimicrobial polyiodinated resin and solvent containing 12.0% wt./wt. antimicrobial resin is prepared and allowed to stabilize for approximately 24 hours prior to use, with a THF:acetone ratio of 2:5.
2) The mixture is stirred at a speed of 200-300 rpm depending upon the vessel volume with the stirring continuing during the dipping.
3) The catheter is dipped into the antimicrobial solvent mixture at a rate of approximately 3-4 inches per minute and extracted from the mixture at a rate of between 2-3 inches per minute.
4) Upon complete extraction, the catheter is rotated in the horizontal position in order to allow adequate evaporation of the solvent blend. The catheter is rotated for 5 minutes to facilitate evaporation and then allowed to dry prior to application of additional coatings of antimicrobial resin.
5) This dip/dry step is repeated until the desired quantity of antimicrobial resin is applied to the catheter. See FIG. 7.

The following results show microbiological data obtained with latex materials manufactured using the process described above.

Example 1

Zone of Inhibition Studies—Polyiodinated Resin Coated Catheters

The antimicrobial efficacy of the polyiodinated resin coated catheters (latex) of the present invention were determined using the bacterial challenge, *Staphylococcus aureus* ATCC 6538. Small segments of the polyiodinated resin coated catheter or a control catheter (no polyiodinated resin) were placed on 1 cm$^2$ swatches of duct tape in an agar plate containing the challenge organism. After the required incubation time, the inhibition zone represented by a clear zone in the bacterial lawn surrounding the antimicrobial-containing article was readily obtained. A zone of inhibition is a region of the agar plate where the bacteria stop growing. The more sensitive the microbes are to the test article, the larger the zone of inhibition. In the two studies, the control catheter did not show a zone of inhibition whereas the iodinated resin coated catheter showed a zone of inhibition of 3 mm.

The following results show additional microbiological data obtained latex materials manufactured using the process described above.

Example 2

Antimicrobial Properties of Iodinated Resin Coated Catheter

The antimicrobial efficacy of the antimicrobial catheters of the present invention was determined using a bacterial adherence assay (Jansen B. et al. "In-vitro efficacy of a central venous catheter complexed with iodine to prevent bacterial colonization" Journal of Antimicrobial Chemotherapy, 30:135-139, 1992). Accordingly, polyiodinated resin coated catheter (latex)-pieces were incubated in bacterial suspensions of *P. aeruginosa* for contact times of 24, 48, 72 or 96 hours followed by enumeration of adherent bacteria on the catheters using the colony count method. *Pseudomonas aeruginosa* is considered an excellent model for evaluation of efficacy due to its ruggedness and its resistance to antimicrobial agents. All polyiodinated resin coated catheters were coated with a 15% antimicrobial solution of triiodinated resin (4 micron) in acetone/tetrahydrofuran solution. Control experiments were run either with untreated (blank) catheters or commercially available silver-treated latex catheters (Bardex I. C. with Bard hydrogel and Bacti-Guard silver alloy coating).

The results of the study indicate that the polyiodinated resin-coated catheters inhibited the adherence of bacteria for the duration of the test. On the other hand, silver-treated catheters showed little inhibitory effect on bacterial growth.

The invention claimed is:

1. An elastomeric medical device that reduces the development of device-associated urinary tract, respiratory and bloodstream infections cause by one or more microorganisms, the device comprising:
   a medical device having an inner surface and an outer surface, wherein said outer surface is coated with an aromatic polyether-based thermoplastic polyurethane in a tetrahydrofuran solution to form a barrier when dried;
   an exterior surface of the barrier comprising one or more polyiodinated resins coated thereon, said one or more resins having a base polymer comprising an anion exchange resin, each of said resins being dispersed in a tetrahydrofuran/acetone solution of polyurethane;
   wherein said one or more resins are allowed to dry to form a solid outer coating;
   wherein the barrier serves to prevent leaching and to control a release of active ingredients of said one or more resins of the medical device for antimicrobial efficacy;
   wherein said solid outer coating releases a polyiodide anion from said anion exchange resin which on contact with one or more microorganisms, exerts a toxic effect thereon without being toxic to a user;
   the release of said polyiodide anion only occurring when said one or more microorganisms, being drawn to the iodine, makes contact therewith, thereby avoiding spontaneous release of active ingredients and enabling sustained availability of said active ingredients; and
   wherein said contact results in a 4 log reduction of said microorganisms.

2. The device of claim 1, wherein said aromatic polyether-based thermoplastic polyurethane in a tetrahydrofuran solution comprises a 2.5% wt./wt. polymer solution in tetrahydrofuran.

3. The device of claim 1 further comprising a binder layer comprising a thermoplastic and hydrophilic polyurethane between said barrier and said solid outer coating to bind said resin to the barrier, said thermoplastic and hydrophilic polyurethane comprising a 1.5% wt./wt. polymer solution in tetrahydrofuran.

4. The device of claim 1, wherein the inner surface of said medical device is coatable with one or more polyiodinated resins comprising an anion exchange resin.

5. The device of claim 4, wherein the inner surface of said medical device comprises an iodinated resin concentration in the range from about 1 g/m2 to about 50 g/m2.

6. The device of claim 1, wherein the solid outer coating comprises an iodinated resin concentration in the range from about 1 g/m2 to about 50 g/m2.

7. The device of claim 1, wherein the solid outer coating has a thickness in the range of about 5 µm to about 250 µm.

8. The device of claim 1, wherein the solid outer coating further comprises one or more different polyiodinated resins and concentrations thereof so as to confer different levels of biocidal activity.

9. The device of claim 1, wherein the medical device comprises a catheter.

10. The device of claim 1, wherein the medical device comprises latex.

11. The device of claim 1, wherein the medical device comprises a pliable substrate.

12. The device of claim 1, wherein the solid outer coating releases a lethal dose of nascent polyiodide anion in less than 3 seconds in a user having a body temperature of about 36.9° C.

13. A method of providing an implantable device having a thermoset uncross-linked polyiodide coating for inhibiting infection induced during use thereof, the method comprising the steps of:
   providing an implantable device having an inner surface and an outer surface;
   applying an aromatic polyether-based thermoplastic polyurethane in a tetrahydrofuran solution to said outer surface of the implantable device to form a polyurethane coating when dry;
   applying a thermoplastic and hydrophilic polyurethane in a tetrahydrofuran solution to an exterior surface of said polyurethane coating to form a binder layer when dry;
   applying one or more polyiodinated resins to the binder layer via a suspension in a tetrahydrofuran/acetone solution, said one or more resins comprising a polyiodide anion delivered from an anion exchange resin; and
   drying the one or more polyiodinated resins to produce an antimicrobial coating on the implantable device that provides for a controlled release of iodine, said antimicrobial coating releasing said polyiodide anion only upon contact with one or more microorganisms, thereby enabling a sustained availability of said polyiodide anion on said coating to ensure at least a 3 log reduction of said microorganisms for prolonged protection against microbial infections.

14. The method of claim 13, wherein the resin application step and resin drying step can be repeated until a desired thickness of antimicrobial coating on the implantable device is achieved.

15. The method of claim 13, wherein the resin drying step is accomplished without heat.

16. The method of claim 13, wherein the resin drying step is accomplished by heating below 80° C. for no more than 20 minutes.

17. The method of claim 13, wherein the resin application step comprises dipping.

18. The method of claim 13 further comprising the step of applying an iodinated resin to said inner surface of the implantable device, wherein the inner surface of said implantable device comprises an iodinated resin concentration in the range from about 2 wt. % to about 25 wt. %.

19. The method of claim 14, wherein the resin application step and resin drying step yields an iodinated resin concentration in the range from about 5 wt. % to about 15 wt. %.

20. A method of providing an implantable device that reduces the development of device-associated urinary tract, respiratory and bloodstream infections caused by one or more microorganisms during use thereof, the method comprising the steps of:
   applying one or more coatings comprising a thermoplastic and hydrophilic polyurethane in a tetrahydrofuran solution to an implantable device and allowing the one or more coatings to dry, whereby a polyurethane-coated implantable device is formed;
   applying at least one polyiodinated resin comprising a polyiodide anion delivered via anion exchange resin to the polyurethane-coated implantable device via a suspension in a tetrahydrofuran/acetone solution; and
   allowing the at least one polyiodinated resin to dry to produce an antimicrobial coating on the implantable device that provides for a controlled release of iodine, said antimicrobial coating releasing said polyiodide anion only upon contact with one or more microorganisms, thereby enabling a sustained availability of said polyiodide anion on said coating to ensure at least a 3 log reductions of said microorganisms for prolonged protection against microbial infections.

21. The method of claim 20, wherein the resin application step further comprises the step of applying versions of polyiodide anion ($I^3$, $I^5$, and $I^7$) in multiple layers to tailor delivery and potency of the antimicrobial coating.

* * * * *